(12) United States Patent
Tsoukalis

(10) Patent No.: US 10,335,540 B2
(45) Date of Patent: Jul. 2, 2019

(54) PHARMACEUTICAL BLEND INFUSION THEREOF AND PARKINSON'S DISEASE MONITORING SYSTEM

(71) Applicant: MICREL Medical Devices S.A., Gerakas (GR)

(72) Inventor: Achilleas Tsoukalis, Gerakas (GR)

(73) Assignee: MICREL MEDICAL DEVICES S.A., Gerakas (GR)

( * ) Notice: Subject to any disclaimer, the term of this patent is extended or adjusted under 35 U.S.C. 154(b) by 1106 days.

(21) Appl. No.: 13/864,927

(22) Filed: Apr. 17, 2013

(65) Prior Publication Data

US 2013/0274654 A1 Oct. 17, 2013

(30) Foreign Application Priority Data

Apr. 17, 2012 (GR) .............................. 2012100215
Oct. 10, 2012 (EP) .................................... 12188029

(51) Int. Cl.
*A61M 5/14* (2006.01)
*A61M 5/142* (2006.01)
(Continued)

(52) U.S. Cl.
CPC ............ *A61M 5/142* (2013.01); *A61M 5/172* (2013.01); *A61M 5/1723* (2013.01);
(Continued)

(58) Field of Classification Search
CPC ............ G06F 19/3468; A61M 5/1723; A61M 2205/502; A61M 2205/58;
(Continued)

(56) References Cited

U.S. PATENT DOCUMENTS 2,876,370 A 3/1959 Pleuger et al.
3,888,250 A * 6/1975 Hill ..................... A61M 1/3679
210/494.1
(Continued)

OTHER PUBLICATIONS

Maetzler, MD, Walter, et al., "Quantitative Wearable Sensors for Objective Assessment of Parkinson's Disease," Movement Disorders, 2013, vol. 00, No. 00, pp. 1-10.
(Continued)

*Primary Examiner* — Amber R Stiles
(74) *Attorney, Agent, or Firm* — Duane Morris LLP; J. Rodman Steele, Jr.; Gregory M. Lefkowitz

(57) ABSTRACT

The invention relates to a system for administering drug to a Parkinson's disease patient comprising (a) a drug; (b) a storing bag for the drug; (c) a pump for administering the drug; (d) a pump controller for controlling the pump activity, the pump controller having access to a correlation of a first parameter $t_x$ and a second parameter $A_t$, and to the current first parameter $t_x$, wherein the first parameter $t_x$ is correlated with a certain activity of the patient and the second parameter $A_t$ is correlated with a dosage of the drug and the pump controller controls the pump activity in dependence of the first parameter $t_x$ and the correlation, and/or wherein the system comprises (e) a storing hag the drug suitable for pre-filling and long-term oxidations-free storage having a multi layer wall with the internal layer made of EVA or cyclic polyolefines and at least one further layer made of EVOH.

21 Claims, 2 Drawing Sheets

(51) Int. Cl.
*A61M 5/172* (2006.01)
*G06F 19/00* (2018.01)

(52) U.S. Cl.
CPC . *G06F 19/3468* (2013.01); *A61M 2205/3569* (2013.01); *A61M 2205/502* (2013.01); *A61M 2205/58* (2013.01); *A61M 2205/60* (2013.01)

(58) Field of Classification Search
CPC ...... A61M 2205/60; A61M 2205/3569; A61M 5/16831; A61M 5/142; A61M 5/172
See application file for complete search history.

(56) References Cited

U.S. PATENT DOCUMENTS

| | | | | |
|---|---|---|---|---|
| 4,457,751 | A * | 7/1984 | Rodler | A61M 5/1723 604/66 |
| 4,624,661 | A | 11/1986 | Arimond | |
| 4,892,604 | A * | 1/1990 | Measells | A61J 1/10 156/244.24 |
| 4,940,465 | A * | 7/1990 | Theeuwes | A61M 31/002 424/409 |
| 5,066,290 | A * | 11/1991 | Measells | A61J 1/10 128/DIG. 26 |
| 5,139,028 | A * | 8/1992 | Steinhaus | A61B 5/0006 600/508 |
| 5,297,234 | A * | 3/1994 | Harms | A23L 3/365 392/379 |
| 5,635,213 | A | 6/1997 | Nystrom et al. | |
| 2003/0114836 | A1* | 6/2003 | Estes | G06F 19/00 604/890.1 |
| 2004/0028613 | A1* | 2/2004 | Quay | A61K 45/06 424/45 |
| 2004/0043043 | A1* | 3/2004 | Schlyter | A61K 9/0095 424/400 |
| 2005/0240147 | A1* | 10/2005 | Makower | A61B 17/24 604/96.01 |
| 2007/0016171 | A1* | 1/2007 | Podvin | A61M 5/141 604/891.1 |
| 2007/0071925 | A1 | 3/2007 | Smith et al. | |
| 2007/0249952 | A1* | 10/2007 | Rubin | A61B 5/0476 600/544 |
| 2008/0051459 | A1 | 2/2008 | Nyholm | |
| 2009/0036951 | A1 | 2/2009 | Heruth et al. | |
| 2010/0042043 | A1* | 2/2010 | Krijnsen | A61M 5/142 604/66 |
| 2010/0106076 | A1 | 4/2010 | Nisato et al. | |
| 2012/0016295 | A1* | 1/2012 | Tsoukalis | G06F 19/00 604/66 |

OTHER PUBLICATIONS

Tsipouras, Markos G., et al., "An automated methodology for levodopa-induced dyskinesia: Assessment based on gyroscope and accelerometer signals," Artificial Intelligence in Medicine, 2012, vol. 55, No. 2, pp. 127-135.

Rigas, George, et al., "Assessment of Tremor Activity in the Parkinson's Disease Using a Set of Wearable Sensors," IEEE Transactions on Information Technology in Biomedicine, 2012, vol. 16, No. 3, pp. 478-487.

Pastorino, M., et al., "Assessment of Bradykinesia in Parkinson's disease patients through a multi-parametric system," 33rd Annual International Conference of the IEEE EMBS (Engineering in Medicine and Biology Society), 2011, pp. 1810-1813.

Tsipouras, M.G., et al., "An Automated Method for Levodopa Induced Dyskinesia Detection and Severity Classification," IFMBE Proccedings, 2010, vol. 29, pp. 592-595.

Tsipouras, Markos G., et al, "On Automated Assessment of Levodopa-Induced Dyskinesia in Parkinson's Disease," 33rd Annual International Conference of the IEEE EMBS (Engineering in Medicine and Biology Society), 2011, pp. 2679-2682.

Cole, Bryan T., et al., "Dynamic Neural Network Detection of Tremor and Dyskinesia from Wearable Sensor Data," 32nd Annual International Conference of the IEEE EMBS (Engineering in Medicine and Biology Society), 2010, pp. 6062-6065.

* cited by examiner

PHARMACEUTICAL BLEND INFUSION THEREOF AND PARKINSON'S DISEASE MONITORING SYSTEM

This application is a utility application which claims the benefit of prior foreign application number GR 2012100215, filed Apr. 17, 2012, and prior foreign application number EP 12188029.8, filed Oct. 10, 2012, the entire contents of both applications are hereby incorporated by reference.

The invention relates to a system for administering drug to a Parkinson's disease patient comprising (a) a drug; (b) a storing bag for the drug; (c) a pump for administering the drug; (d) a pump controller for controlling the pump activity; the pump controller having access to a correlation of a first parameter $t_x$ and a second parameter $A_t$, and to the current first parameter $t_x$, wherein the first parameter $t_x$ is correlated with a certain activity of the patient and the second parameter $A_t$ is correlated with a dosage of the drug and the pump controller controls the pump activity in dependence of the first parameter $t_x$ and the correlation, and/or wherein the system comprises (e) a storing bag the drug suitable for pre-filling and long-term oxidations-free storage having a mufti layer wall with the internal layer made of EVA or cyclic polyolefines and at least one further layer made of EVOH; and (f) optionally sensors and analyzing their data means, providing therapy results feedback.

Patients with advanced Parkinson's disease, depend on ingesting or on infused medicines in order to have normal mobility. Otherwise they may freeze—remain motionless or can hardly moove (bradykinesia), increased dosage on the other hand, creates hyper-mobility called dyskinesia annoying them greatly.

A method is reported, in the state of the art, for the preparation of a drug, as well as a method for the continuous administration to patients suffering from advanced Parkinson's disease (AP) via a portable pump U.S. Pat. No. 5,635,213, US2008/0051459, sub-abdominally in the duodenum, in the small intestine through the use of a catheter, or nasally for 18, 24 or more hours. The inventor of the pharmaceutical mix Levodopa-Cabridopa, Neopharma Production AB, was bought by Solvay Pharmaceuticals GmbH, which in its turn was bought by ABBOTT, the latter completing successfully the 54 weeks phase III clinical trials for the Duodopa formulation in 2011.

In the state of the art as well as commercially, a SMMS/Deltec CADD/Legacy pump is used and a drug bag by the same company referred to in the user's manual as being manufactured of PVC material. The drug bearing the commercial name Duodopa has been marketed by ABBOTT in pre-filled bags from the above company.

It is a known fact that the pharmaceutical substance LEVODOPA (the main therapeutic component of this drug) is easily oxidised, and for this reason in the U.S. Pat. No. 5,835,213 patent it is reported that a high viscosity medium is used to suspend the LEVODOPA micro-spherules in order to prevent the aspiration of air in the bag. The bag's PVC material, being a known fact, permits ambient air permeability and for this reason deep freezing down to −48° C. is used when distributing the drug from the manufacturer's site to the pharmaceutical warehouses, the temperature increasing gradually to −17° C. before reaching the user and employing simple refrigeration thereon before the end use, a very costly process in all.

In the treatment of advanced Parkinson's Disease, the therapeutic substance Apomorphine (6aR)-5,6,6a,7-tetrahydro-6-methyl-4H-dibenzo(de,g)chinolin-10,11-diol is used in its liquid form, having the molecular formula $C_{17}H_{17}NO_2$, usually administered via syringe pumps.

It is known in the state of the art that in the last decade, multi-layered membranes were invented for the packaging of food and medicine, having internally a plastic layer suitable for contact with drugs as well as various other layers preventing the transport to and from of gases, like oxygen and carbondioxide, of wafer vapor and filtering UV radiation.

It is also known that additional protection is obtained by using a single overall multilayered packaging for the whole bag, comprising at least aluminium and one flexible plastic sheet laminated and by modified atmosphere packaging of the drug in the bag usually with Mitogen inert gas (substitute of oxygen), known in the packaging of food, etc.

The present-day infusion pumps for Duodopa/Apomorphine can be programmed in order to provide a stable flow, being also equipped with an extra-dose button in case patient has difficulty in moving. It is known that this existing solution is better than the sequence of injections, or pills for advanced Parkinson's disease; however, it does not resolve the problem of normal patient mobility.

Accelerometers are also known in the art as well as body inclination meters (inclinometers) or gyroscopes measuring trembling, bradykinesia, dyskinesia, body posture (lying down or upright), rotations—dancing movements. A lot of work-studies have been published, relating to sensors and their signal processing, detecting the mobility-related problems of patients with Parkinson's disease. The implementation of this research work may provide help according to the present patent, allowing correction of the medication dosage and functioning as a feedback to the attending physician.

It is the object of present patent to provide a system for administering pharmaceutical substance, in a pre-filled bag with protection against oxidation for long-term, low-cost maintenance and/or a pump bearing easy and/or effective programming characteristics for the treatment of Parkinson's disease. Further it should be possible that sensors are added to the system to give feedback to the attending physician regarding the right dosage and the possibility to regulate it from a distance in order to optimize patient's mobility.

This object is solved by a system for administering a drug to a Parkinson's disease patient comprising (as a drug: (b) a storing bag for the drug; (c) a pump for administering the drug; and (d) a pump controller for controlling the pump activity, the pump controller having access to a correlation of a first parameter $t_x$ and a second parameter $A_t$, and to the current first parameter $t_x$, wherein the first parameter $t_x$ is correlated with a certain activity of the patient and the second parameter $A_t$ is correlated with a dosage of the drug and the pump controller controls the pump activity in dependence of the first parameter $t_x$ and the correlation, and/or wherein the system comprises (e) a storing bag the drug suitable for pre-filling and long-term oxidations-free storage having a multi layer wall with the internal layer made of EVA or cyclic polyolefines and at least one further layer made of EVOH or other strong oxygen and moisture barrier material.

It is an advantage of the system according to the invention that a pump controller can control the pump activity dependent on the activity of the patient and on a specific dosage that is correlated with this activity. The advantage of the preferred storing bag for the system according to the invention is that it ensures that the respective drug can be stored over a song time even at room temperature. This can give advantages because the drug consumption is depending on the actual activities of the patient. Therefore, there can be a synergetic effect of a combination of the preferred bag with the specific pump controller system since stability of the drug will not be the limiting factor even in case that the patient only makes activities that need only low dosage of the drug.

According to the invention it is preferred that the storing bag for the drug comprises internal micro-striation texture.

This micro-striation ensures that the drug from the bag is easily available for the pump.

a) According to present invention the pharmaceutical formulation may comprise a solution of various components (active ingredients) e.g. Levodopa (2S)-2-amino-3-(3,4-dihydroxyphenyl)propanoic acid having the molecular formula $C_2H_{11}NO_4$ and/or optionally Carbidopa (2S)-3-(3,4-dihydroxyphenyl)-2-hydrazinyl-2-methyipropanoic acid having the molecular formula $C_{10}H_{14}N_2O_4$, and/or Benserazide 2-amino-3-hydroxy-N'-[(2,3,4-trihydroxyphenyl)methyl]propanehydrazide having the molecular formula $C_{10}H_{15}N_3O_5$.

The liquid formulation as described in the state of the art can be administered to the digestive tract, either via catheter and body incision or via the nasal cavity through a pump for the required time interval, equal, greater, or less than 24 hours.

According to another aspect of the present invention the preferred pharmaceutical substance is the generic drug Apomorphine (6aR)-5,6,6a,7-tetrahydro-5-methyl-4H-dibenzo(de,g)chinolin-10,11-diol, having the molecular formula $C_{17}H_{17}NO_2$, administered subcutaneously.

b) This liquid solution in the present patent is preferably pre-filled, in an inventive way, in 100 ml volume or less preferred multilayered bags, in order to achieve long-term pharmaceutical formulation storage, thus avoiding the risk of oxygen take up that induces drug degradation. Said multilayered bag preferably has an internal layer, made of EVA (Ethylene vinyl acetate) or polyolefins (polypropylene-ethylene) to provide biocompatibility and good stability, and protective layers made of EVOH (Ethylene-vinyl-alcohol, or AlOx (Alumina oxide)—$Al_2O_3$, or SiOx, PCTFE (Polychloro-tri-ethylene homopolymer), or CTFE (Chlorotrifluoroethylene), polyacrylonitrile, or LCP (Liquid crystal polymers), or PVDC (Polyvinylidene chloride), as well as a combination thereof, or even ultraviolet radiation barriers (UV filters) or opaque transparent packaging. There may also be present intermediate barrier layers as adhesive flexible plastic sheets. The flexible material the bag is made of, preferably has internal micro-striations (texture) not allowing the occlusion of the liquid passageways when the bag walls collapse coming together during emptying, in contrast to the smooth materials, thus enabling the use of the pump and eventually the bag itself in any position, enabling the pump to be used in a portable manner. The multilayered bag-infusion tube and tubing set may be filled with drug under air vacuum or nitrogen gas (modified atmosphere packaging) for additional protection during long-term storage. The multilayered bag-drug-infusion tube and tubing set may be packed in turn, inside a package made of plastic and aluminium laminated sheet (of the most potent gases-barrier type).

On account of this packaging, the following advantages may be obtained:

The multilayered bag-drug-infusion tube and tubing set may be packed in turn, inside a package made of plastic and aluminium laminated sheet (of the most potent gases-barrier type). The multilayered bag-infusion tube and tubing set may be filled with drug under air vacuum or nitrogen gas (modified atmosphere packaging) for additional protection during long-term storage.

The infusion can last an entire week without any risk of decomposition of the pharmaceutical mix.

The drug suspension for use in this invention could also be prepared and administrated less viscoous than 7000 mPa·s when measured at low shear rate with a Brookfield viscometer LVDV-II+ series, spindle LV#1, 2 rpm speed, 21° C., since there is no need for protection against oxidation through fluid density, facilitating flow along with a lower battery consumption and a longer fasting infusion mechanism due to a lower operating pressure (lower hydrodynamic pressure. In case of doubt (if the above method cannot be applied) viscosity is measured according to ASTM 02196-10 Standard Test Methods for Rheological Properties of Non-Newtonian Materials by Rotational (Brookfield type) Viscometer.

Accordingly, a preferred system according to the present invention is a system, wherein the drug comprises (active ingredients) Levodopa and/or Carbidopa and/or benserazide, preferably present in the formulation in concentrations from 0.01 up to 20% w/w preferably in the form of microscopic particles more preferably encapsulated in microspheres, suspended a viscous aqueous medium of plastic or pseudoplastic nature of viscosity range 300 to 7000 mPa·s measured at a moderate shear rate (20 $s^{-1}$-500 $s^{-1}$). This aqueous carrier is an aqueous dispersion of a water swellable colloid of carbonhydrate or polysaccharide or synthetic nature.

The formulation for use in this invention may contain other additional agents/excipients, i.e. stabilizers, antioxidants, preserving agents, pH and osmolality regulating agents, thickening agents, colorants, buffering agents, bacteriostats.

c) To achieve the largest possible dosing accuracy, the pump accessory inventively has an infusion mechanism tube having a thick silicone wall, allowing for the development of a large suction vacuum at −0.8 bar, necessary for viscous fluids.

Moreover the pump of the present invention provides a correction for the motor speed, in order to compensate for under-infusion due to the exceptionally dense drug, in other words for each infusion rate, the % loss in accuracy in statistical measurements, is compensated for by a proportional increase in the motor speed in order for the real Infusion to be very precise.

d) Patients with advanced Parkinson's disease cannot move around without pharmaceutical treatment. If the drug is not sufficient for their exhibited level of activity, they are presented with difficulty in movement, immobility, and in case it is more than required, they exhibit dyskinesia performing dancing movements, thus getting very annoyed. For this reason the present invention offers a solution in the planning of the patient's activities, mapping; them through the administration of the corresponding drug-dose infusion, in order for his life to be as near to normal as possible. The patient should be aware to program the change half an hour before the next activity, the reason being that the drug needs half an hour to 45 minutes to take effect and bring him to the desired mobility level, as we will be detailed below. Analyzing statistics from existing patients, we have found that they usually live very programmed lives, with seldom changes, and thus the present patent attempts to make pump scheduling as easy as possible, for both existing and oncoming activities. Pump programming is analogous to activity, however, because it requires regulation patient- and time-wise and this regulation is an ever-continuing process of controlling the results and reprogramming, it is separated inventively from the activity planning which is more deterministic. Thus the patient has the main say in planning his activities and the physician (perhaps the patient as well) in the infusion parameters regulation as will be analyzed below.

In the present patent we introduce the concept of an activities timetable. The pump in the present patent preferably has a real time clock, for scheduling a different, infusion rate depending on the time of the day and planned events such as special activities, sleeping or awakening time or siesta, sitting down to watch tv or do some reading, walking etc.

The scheduled events may be different for the Weekends, feasts etc., that is to say we introduce by the present invention the meaning of annual planning—timetable which is not necessarily stored in the pump, but at any point in the network, and preferably only part of it is sent to the pump.

The mobility planning may be done by the patient or his assistants and includes a series of levels presenting increasing mobility, e.g. $t_1$=lying down, $t_2$=sitting, $t_3$=walking, $t_4$=increased movement e.g. gardening. Updating the timetable may be carried out on the pump if it is equipped with a screen of sufficient analysis, or through a tablet or mobile smart phone or computer connected to the internet, excluding the pump that may function autonomously. The activity may be analyzed on an hourly basis, with bars on the screen showing the activity level of a certain hourly time interval. Moving the bars up and down, one may correct/schedule the activity, moving the bar to the right elongates the activity in time to the next hourly intervals for easier scheduling. Having finished with day scheduling the system may ask whether the changes made are temporary or permanent. If permanent, then an algorithm of artificial intelligence may make an "intelligent" merge of the new data along with the previous changes and updates the annual plan, or if it is made for the first time if brings on to the screen the 380 day planning. The algorithm may pick up information from the internet on holidays as well as religion in the relevant region and handles it as a separate section. The user habits on specific dates may be recorded as periodic exceptions. The patient may be able to change in real time the daily program through the pump, the detachable screen thereof, his mobile phone or tablet or computer, in case of emergencies and when the pump is connected to a Remote server like MicrelCare of Micrel Medical Devices lit may become synchronized.

e) The dosage that is to say the infusion rate in ml/hr necessary for achieving the above scheduled mobility, is regulated algorithmically, utilizing a series of parameters as will be described below, the first being the level of the described activity, one parameter A corresponding to each and every level.

Dosage is proportional to the range of activity as well as the passage from one level of activity into another plus a time lead due to the delayed action of the drug (30'-45'). This dosage regulation, contrary to the activity planning is preferably carried out by the attending physician, either on the pump or using telemetry from a distance as will be described below. Parameters A corresponding to activity levels that may have all the intermediate values, e.g. 3,4 or any other value the physician wishes to use that may be mapped in correspondence to a need in medicine for a certain activity. A change in parameter A of an activity, by the physician, by a certain percentage in order to adapt the dosage to the patient needs, in case the dosage and the activity share a linear relationship according to the following, the dosage may get to be corrected throughout the annual plan for this activity, in other words the patient schedules activities in the timetable in an absent minded manner; sleeping, seating, walking, gardening, these are mapped/take an initial value for relative muscle work intensity parameter A: 1, 2, 3, 4 (dependent from the activity $t_x$) and the physician adjusts parameters A to the precise value for the suitable dosage, this is a continuous control/change procedure (trial and error) for the optimum adjustment. One can enter as many activity levels as is necessary or each one by its name and its correlation to parameter A.

According to the above it is preferred that the system according to the invention is arranged in a way that the first activity parameter $t_x$ can be amended by the patient while (infusion control) parameters a, b and $A_t$ can be amended by the attending physician and/or a by a control system that is in contact with the system.

The present specification provides optionally on this, an infusion system, occasionally or permanently connected to the internet, through WiFi incorporated in the pump for permanent connection, or NPC/RFID for localized communication-connection via a mobile phone, or connection to a pump-sensors communicating charger for periodic connection, or a special mobile phone by our company permanently connected through GSM/GPRS to the Micrel Medical Devices telemedicine system commercially called MicrelCare™, wherein the treatment may be monitored and controlled by the attending physicians, with serious advantages to the treatment as will be analyzed below.

Accordingly it is preferred that the system according to the invention comprises (f) means for therapy feedback measurement and report and/or (g) recording and monitoring infusion and feedback means, and/or (h) remote therapy regiment adjustment means.

With this the dosage regiment can be remote controlled by a physician and/or by an automated control system.

For this purpose it is further preferred that the system according to the invention comprises an interface for submitting data to a remote control system and/or a remote data storage unit and/or the attending physician and/or that the system further comprises an interface for receiving data from a remote control system and/or a remote data storage unit and/or the attending physician.

f) it is further preferred that the system according to the invention comprises means for measurement of the status of the patient. Those means may preferably be selected from the group 3D accelerometer, gyroscope, electromyogram, and bed foil with sensing of movement, heart rate and/or respiration during sleep capability.

The system may preferably be supplemented with the optional use of movement sensors, comprising accelerometers and a gyroscope during the day or even a movement-, heart rate- and respiration-sensing mattress during the night. These preferably energy-autonomous sensors may bearbatteries and local microcomputer on one or two wrists (as bracelets-watches) and ankles (or pinned to slippers) sense in an absolute synchronisation of their waveforms, the trembling movements or the immobility, and following robotic analysis as will be described below of the combined signals, and in optional combination with a gyroscope sensing dancing hyperkinesia movements LID (Levodopa Induced Dyskinesia), the extended pump system of the present invention preferably analyzes dyskinesia, bradykinesia, ON/OFF, trembling and the results and the measurements from the mattress during night time may be dispatched once a day to the monitoring system server of the present patent, in order to record the therapeutic result. The infusion recording preferably in the form of a graph in the present invention may be mapped against the therapeutic result—treatment feedback which is the sensor data analysis, as well as the answers to questions addressed to the patient or his family and relatives regarding side effects i.e., constipation, nausea, grainy tissue, dyskinesia, insomnia, irritation of the catheter wound, stress etc.

The attending physician or an autonomous system of artificial intelligence, based on this information, can make a decision on the treatment correction (parameters a, b, A below as well as other medical advice) in order to minimise the side effects and to maximise the therapeutic outcome.

Accordingly a preferred system according to the present invention comprises an input interface for a response of the patient to questions asked by the patient's feedback function.

It is further preferred that the system according to the invention comprises means for detecting malfunction of the system.

Having the above in mind it is further preferred that the system according to the invention is arranged in a way that in case of negative feedback by the patient, critical status of the patient and/or malfunction of the system the respective information is automatically submitted to a remote control system and/or a remote data storage unit and/or the attending physician.

FIGURE LEGENDS

FIG. 8 Shows a parameter a (α) possible decaying function graph per volume and FIG. 8' per time passed till morning wake up. This is a curve fit to patient's feedback by means of questions answered or sensors reporting treatment results.

A PREFERRED EMBODIMENT OF THE INVENTION

Figure 1:
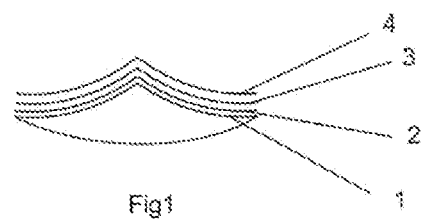
FIG. 1 Shows the potential stratifications of a multi layered flexible plastic bag.

The present invention provides a pharmaceutical solution for advanced Parkinson's disease, in two different versions and corresponding basic pharmaceutical substances and a different administration path for each of them, as is reported hereinabove, in combination with a prefilled bag of drug made of a flexible plastic sheet with oxygen/carbon dioxide/humidify transport protection in order to prevent drug oxidation and/or concentration change. This sheet consists of 2 or more layers, as in FIG. 1 wherein the internal side (1) is preferably EVA or polyolefin with cross-wise micro-striations for easy emptying, a connecting sheet (2) follows, an EVOH gas barrier (3) preferably follows, as well as protective structure or binder to other layers (4), the no. of layers reaching even 7 depending on the combination of materials.

Figure 2:
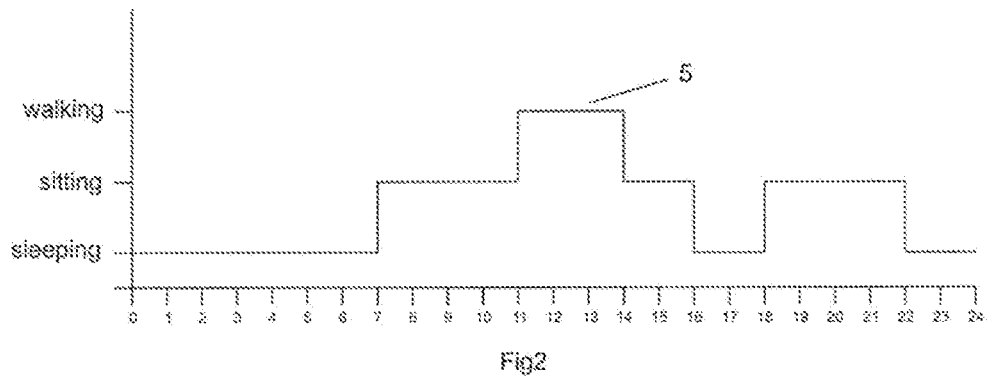
FIG. 2 Shows a daily schedule of activities on the part of the patient with names and on the part of the physician with numbers on dose regulation parameters A.

The planning—timetable of daily activities from the patient can be formed realistically every day FIG. 2 (5) and it may include only one rolling day changing according to the needs, or one year wherein the changes need statistical analysis and artificial intelligence support in order to merge with the existing timetable and anticipate the next day as accurately as possible and propose it to the patient for easier data entry. The patient of course can alter in real time his immediate schedule by raising or lowering the activity bar on touch screens, and its time duration by pulling it to the right—left according to the need in hand, the places being distinguishable and having written adjacent to them the activity type for each level, in an alternative simple (no touch) screen, the type of activity is selected from a list as well as the time/duration, the simple screen then displays the altered day schedule or the next 24 hrs. The follow-up of daily activity via user as well as sensor information dispatched and recorded in the server, forms a realistic rolling, weekly or yearly, activities schedule replacing the initially planned one, with the help of algorithmic or artificial intelligence not described herein, in the data merging or not.

Communication with the user can be carried out through the pump or a mobile application. The result is to program the pump using telemetry or locally as regards the real user activity and to minimise dyskinesia, trembling etc.

The drug infusion for a constant activity according to the medical practice is constant and depends proportionally on the required work level.

According to the invention a system is preferred wherein the controller further has access to a parameter "a" for a master volume control, wherein the controller controls the pump infusion Rate (pump activity) by a multiplication of the parameter "a" with the second "Relative muscle work intensity level" parameter "$A_t$" that is correlated with the first activity level parameter "$t_y$".

The meaning of the parameter "a" is a factor for infusion amount needed for a certain muscle work, as a general factor for all activity levels in ml/hr. This general factor controls overall infused volume per day by multiplication with the factors $A_t$ which change during the day according to mobility calendar.

The infusion algorithm regulates transiently a higher infusion in order to increase the activity before it is realised due to the delayed drug action. Correspondingly infusion reduction before the activity reduction, e.g. higher infusion before waking up in the morning, infusion reduction before going to bed, or an increase before the daily increased activity. In addition, the user has the possibility of taking a bolus dose. After the transient part in preparing for the next activity, the infusion is constant.

According to the invention the system is further preferred wherein the controller has further access to a (bolus volume) parameter "b", wherein the controller controls the pump activity in case of a change of the first parameter by a multiplication of parameter b with the difference between the second parameter $A_{t+z}$ that is correlated with the first parameter $t_{+z}$ after the change and the second parameter $A_{tx}$ that is correlated with the first parameter $t_x$ before the change to amend the dosage z minutes prior to the change by adding the result of the multiplication ($b*(A_{t+z}-A_{tx})$) to the dosage according to $A_{tx}$.

The simpler form of the novelty in the technique of algorithmic planning is the following and consists of a first part of constant infusion proportional to the activity level and a transient part (replacing the bolus dose, however, not in an obligatorily manner) in preparation for the next taking into account the delayed action of the drug:

$$E_{tx} = *A_{tx} + b*(A_{t+z} - A_{tx})$$  Equation 1, wherein

E is the infusion profile including rate in ml/hr in time $t_x$ as a positive value or zero and bolus volume at z time before activity change $A_t$ is dosage of the drug relative to patient's muscle work intensity level one for each calendar patient's activity/mobility type a factor for infusion Rate needed for correct kinetic performance at any mobility level, as a general factor for all the activity and adjustment levels in ml/hr.

b Bolus factor for the automatic leading dose (increase/decrease) for the transient activity situation from one level to the next given, a time before activity change $t_x$ is the mobility type at the real present time (x according to scheduled calendar)

z is the time delay of the drug action, preferably 30-45 min, being constant for each different drug and infusion path.

t+z is scheduled mobility type after mobility type at real present time.

$a*A_t$ is equal to the steady state infusion rate necessary for an activity t.

For example, if the daily average drug consumption during 24 hours for medium-type activity is 80 ml, then the medium-type activity, e.g. seating can be A=2, and then the average infusion rate per hour is 60/24=2.5 ml/hr and a=2.5/2=1.25 ml/hr.

The physician should regulate number A=2 relative to the muscle work produced in higher (3) or lower (1) activity, in order not to end up having one activity with too much drug and another with too little as for more muscle work, patient needs more drug per hour.

In the example, number a=1.25 ml/hr is for the Rate of drug needed by the treatment regimen in total, i.e. this will change in case all of the activities are presented with drug deficiency or surplus. In case only one activity is in deficiency, its parameter A only is increased.

Factor b regulates the onset of a subsequent activity with the proper comfort from the first instance. It increases in case the patient is slow in reaching normal functioning, and decreases in case diskinesia phenomena occur even for a short time.

The pump and/or the server compute also the total drug volume that should be in the bag, for a series of parameters and a certain daily scheduling.

Bolus can be positive or negative. In case it is positive, a bolus as known in the art is given at high rate, in case it is negative, infusion is suspended till the amount of Bolus volume is reached, then it continues at whatever level is needed from steady state part of the equation. The pump or server computer may indicate to the physician the value of this integral (dosage volume) for this transient dose thus enabling him to set parameter b property.

Figure 3:
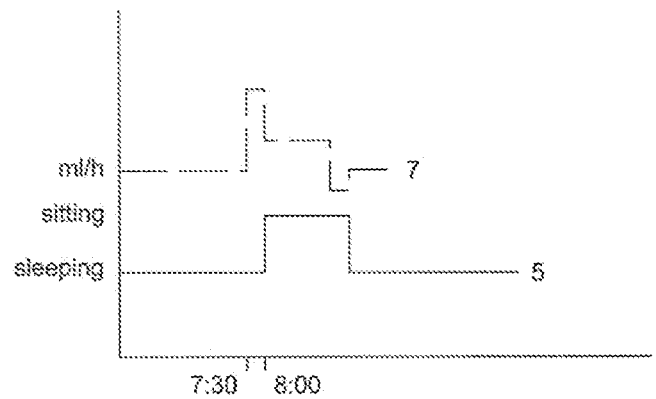
FIG. 3 Shows a planning of few hours and the corresponding pump infusion for a certain adjustment of A, α and β and $_{+z}/t_x$.
Figure 4:
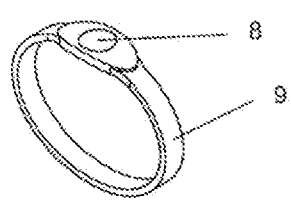
FIG. 4 Shows a hand bracelet with movement sensor.

FIG. 3 (5) shows a scheduled activity in time, and the infusion (7) according to the equation. The patient may be warned, if he so wishes, before the onset of the transients in case he needs to make any modifications on the daily schedule—postpone next activity about x minutes or hours.

Separating the task of activity scheduling to be done by the user and the task of infusion parameters setting by the physician, enables pump programming from a distance without risks. For this reason either the parameters are being entered in the pump or via telemetry, observing however the safety limits in the pump that cannot be exceeded by teleprogramming.

In the present invention as it is reported analytically below, there is provision for effectiveness of treatment feedback to the attending physician via sensors in the present invention, feedback is used as an alternative by the user himself or his family and relatives, via questions programmed in time according to the physician's needs or on demand by the patient at his own will.

Figure 7:
FIG. 7 Shows the infusion results reference range from the patient
Figure 8:
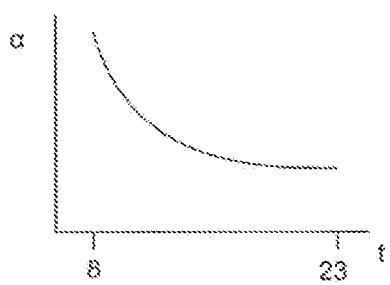
FIG. 8 Shows a version of the electronic blocks of a movement sensor.
Figure 8:
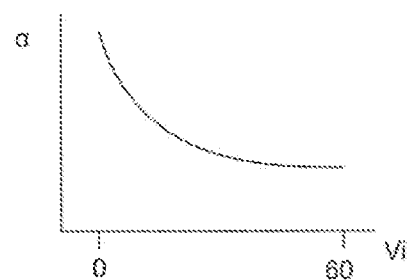

A report on the results (questions-answers) and on the side effects has two legs, the first one is about controlling the infusion properly, with questions on infusion control with quantification, see FIG. 7, and the second one is about the side effects recording;

1. Overall, does infusion promote satisfactory movement, difficulty or hyperkinesia? Draw the bar to the left for a little more infusion, to the right for excessive, depending on how you feel with it.

2. If a certain activity is not properly set, choose that activity from the list, and draw the bar to the left for a little more infusion, to the right for excessive, depending on how you feel with it.

3. Beginning a new activity, do you experience satisfactory mobility, more or less? Draw the bar to the left for a little more infusion in order to get prepared for the oncoming activity, to the right for excessive, depending on how you feel with it.

4. Fill in the square adjacent the word if you have the corresponding side effect with
constipation,
nausea,
grainy tissue,
dyskinesia,
insomnia,
nightmares at sleep
stress
irritation of the catheter wound.

No. 1 helps configure master rote parameter a

No. 2 helps configure each number—of relative activity parameter A

No. 3 helps configure parameter b

No. 4 helps in the recording of the general drug side effects some of which are related to a high or low infusion.

The report can be dispatched to the server when the pump or any other means set to receiving the report is connected to the internet.

To begin with, the physician and as an alternative an algorithmic programming may be receiving as parameters the programmed/updated activity, the administered infusion along with any requests for on demand doses and the recording of side effects (sensors and reports) depending on the dosage given during the previous time interval (case history) plus the physician's corrections from lab observations on kinesiology and personal reports, all stored on the server. The optional algorithm of artificial intelligence not described herein, is continuously being improved in analyzing the effectiveness of the infusion scheduling, towards obtaining the optimum result and suggesting to the physician the most appropriate parameters A, a, b in order to achieve the optimal patient situation.

The recording of all measurements, infusions and reports on web pages in the internet, allows the best possible follow-up in the treatment by the attending physician, plus a proof of the therapeutic effect to third parties, i.e. social security funds, companies etc.

That is to say, according to the present invention a rolling schedule (calendar) on activities is created including also day or night sleep, which is configured using a first algorithm that could also contain neural networks, said algorithm learning from the user's habits, combining them with the time during which they actually take place and in hours of the day and in anniversaries, weekends, holidays, etc. said schedule being enabled to change by the user, adding this way new data to the habits, or change through the sensor's measurements taken on the user's body monitoring its condition in real time.

According to the present invention, by having the updated 24 hour schedule as input, a second algorithm can start operating that could also contain neural networks and PID (Proportional Integral Differential) algorithm for regulating different drug infusion profiles for enteral or nasal or parenteral or transdermal or intramuscular infusion, plus drug type as same or similar to Duodopa as described in the present specification, or apomorphine or the like. The PID reads the error (i.e. kinetic disorders) from the sensors on the patient's body, and remains inactive if sensors have not been activated; however it gets activated in case of reports by the user about side effects or drug activity.

Figure 5:
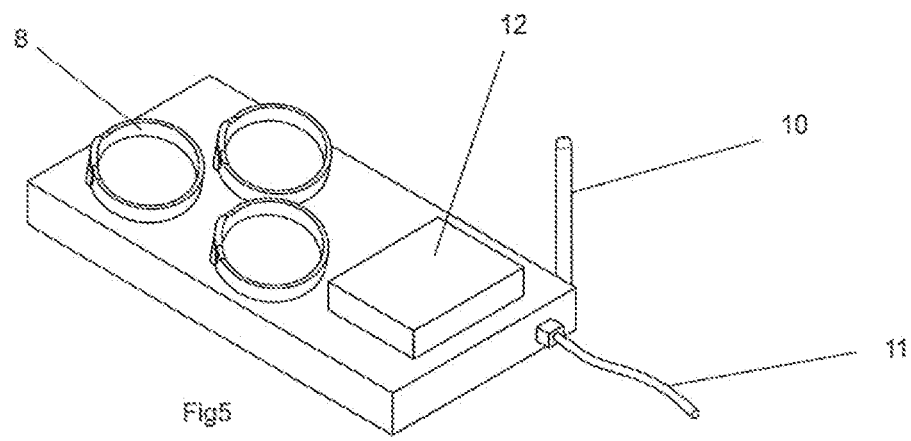
FIG. 5 Shows a sensor and pump battery charger with simultaneous data transfer to a server.

The pump and sensor batteries charger FIG. 5 is connected to the internet, via Ethernet (11) or WiFi (10) or GSM/GPRS, charges the pump only or the alternative battery (12) thereof, in case it is being used on a 24 hours basis, plus sensors (8) during the night, transmitting simultaneously the pump data (incidents as alarms, on demand doses etc) with a time stamp, plus the kinetic behavior daily data of the patient along with the sensor data. Locally or in the server, this data are analyzed using algorithms as described below.

Figure 6:
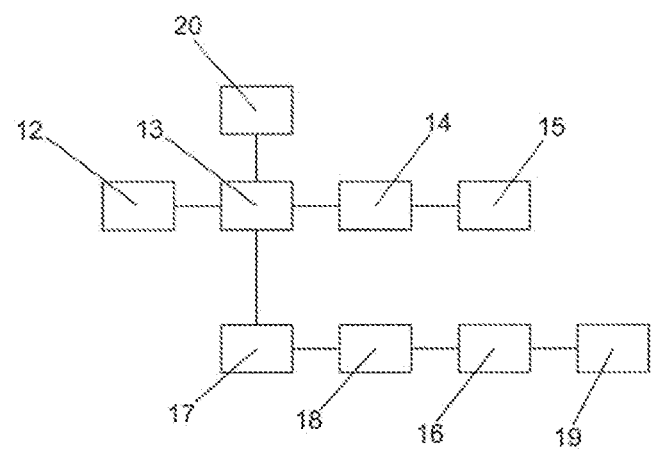

The sensors (8) placed on a hand or leg strap (9) or on a slipper, in the electronic part FIG. 6 preferably have rechargeable batteries (16), charger (18), USS connection (17) for data and power transfer, to/from the microcomputer (13) connected with accelerometer or gyroscope sensor (12), 18 hrs flash data memory (20), WLAN wireless connection ZigBee (14), antenna (15). Gyroscope (with all the above mentioned electronic platform) can be placed on the breast in a clip, in order to detect hyperkinesia situations (patient dancing movements) resulting from any drug overdose.

The sensors preferably have 62.5 Hz sampling, in 3 dimensions x, y, z and being all synchronized, they read any movement the same moment it happens adding to the data a package of some KBs plus the time (from a synchronized clock) in order to enable data processing at a different time and in another computer. Synchronization is initially obtained in the charger base by the home base computer of FIG. 5, via USB, and continues at regular, e.g. 1 minute or more, time intervals via ZigBee, wherein, preferably, one sensor at a time, alternating with the next one, sends a real time clock synchronization signal. On the intermediate intervals the docks are based on the internal crystal for synchronized measurements.

The wrist bands at the hands further may comprise sensors that may be e.g. proximity sensors to detect when wrists come close together. Inventively, when a patient feels that he has a kinetic problem he is instructed to try to raise both hands in a predetermined position e.g. in front of him close one wrist to the other, and when a beep sound is heard he moves them back normally. By doing so, an algorithm for detection of dyskinesia or bradykinesia, or ON/OFF, or tremor, can easier find the type of the kinetic problem, analysing waveforms before and after the proximity receding which for dyskinesia will have a lot of movement detection and for bradykinesia much less movement. The system records the time stamp of the hands proximity for this analysis purpose. The proximity sensor can be of any simple type like a magnet and a reed/hall effect switch, an optic sensor and light source, or simple switch pressed by the other hand therefore a single wrist sensor/switch band can be sufficient. This is a patient activated feedback when he feels bad, so doctor can better understand on a screen the time and type of patient's discomfort for therapy adjustment (parameters a,b,At). This additional option greatly facilitates the certification process of the system, as regulatory wise it is the patient who reports a problem and system analyses its type, rather than having to prove that the system correctly detects any disorder. Also in its simpler form without sensors, the switch can be a feedback of the therapy when patient feels bad, with time stamp on the event.

In the charging bass, the sensors transfer the stored data of the order of 35 MB to their flash drive, in order to be processed locally by the algorithm mentioned below, or the server for processing therein. Finally the server receives the treatment feedback, i.e., whether the patient moved about without any problems or had a problem and what kind of problem, through the charging/processing base, or from its own internal algorithm (in case of dispatched data). Thus the doctor has all the information in order to be able to correct the treatment regimen, and optionally the advice from the second aforementioned treatment analysis algorithm.

The sensor synchronised waveform processing algorithm, attempts to discover through relatively chaotic data, pathological disorders in patient movement owing to improper treatment/infusion. What is required is to correct the treatment with the aid of computing support For this reason an operating algorithm including neural networks able to be trained, compares the results if outputs to the results judged to be right by the expert physician, and thus the neurnal network is trained in clinical trials. The trained artificial neural networks with large clinical data bases corresponding to medical interpretation provide us with the basic factors introduced into the neuronal networks of computing units used in commercial applications.

Before the supervised neural networks, the processing of the results from synchronised 3 axes waveforms is preferably carried out utilizing digital filtering (FIR) and then via a moving window, classification into tree-branching decisions and/or the Random Forest algorithm and analysis via Feature Vectors, or other neural networks with intermediate FIR filters. The objective is finding trembling, bradykinesia, dyskinesia/LID (Levodopa Induced Dyskinesia), ON/OFF situation, according to the following literature.

The combination of algorithms in clinical trial showed reliable results on the patient situation with a precision in the order of 85% with a complete series of sensors and 65% with only one sensor on the hand. According to the present invention, the user in collaboration with his physician decides whether to put one, no one, or all the sensors depending on the annoyance level being able to tolerate as well as the desired treatment level.

Sensor Analysis Literature

An automated methodology for levodopa-induced dyskinesia; Assessment based on gyroscope and accelerometer signals. Markos G. Tsipouras, Alexandras T. Tzalias, George Rigas, Sofia Tsouti. Dimitdos I. Fotiadis, Spires Konitsiotis: Artificial intelligence in medicine 55(2): 127-135 (2012)

Assessment of Tremor Activity in the Parkinson's Disease Using a Set of Wearable Sensors. George Rigas. Alexandres T. Tzalias, Markos G. Tsipouras, Panagiota Bougia, Evanthia E. Tripoliti Dina Baga, Dimitros I. Fotiadis, Sofia Tsouli, Spiros Konitsiotis: IEEE Transactions on information Technology in Biomedicine 16(3): 478-437 (2012)

Assessment of Bradykinesia in Parkinson's disease patients through a multi-parametric system, Pastorino M, Canceta J, Armdondo M T, Pansera M, Pastor-Sanz L, Villagra F, Pastor M A, Martin J A, Cent Proc IEEE Eng Med Biol Soc. 2011:2011:1810-3.

An automated method for Levodopa induced dyskinesia detection and severity classification M. G. Tsipouras, A T. Tzalias, G, Rigas. P. Bougia, D. I. Fotiadis, and S. Konitsiotis, IFMBA proceedings Vol. 29

On automated assessment of Levodopa-induced dyskinesia in Parkinson's disease Tzalias. A. T.; Fotiadis, D. I.; Konitsiotis, S. Engineering in Medicine and Biology Society, EMBC, 2011 Annual international Conference of the IEEE Dynamic Neural Network Detection of Tremor and Dyskinesia from Wearable Sensor Data Bryan T. Cole, Serge H. Roy, Carlo J. De Luca, Life Fellow, IEEE, and S, Hamid Nawabo, Senior Member, IEEE 32nd Annual international Conference of the IEEE EMBS Buenos Aires, Argentina, Aug. 31-Sep. 4, 2010.

Example

The example depicts a scheduled day activity (and resulting pump activity) in Table 1 and the same activity table wherein after a patient's feedback the drug volume for walking (activity $t_3$) was amended.

TABLE 1

| Half hours of a day | 0 | 0.5 | 1 | 1.5 | 2 | 2.5 | 3 | 3.5 | 4 | 4.5 | 5 | 5.5 | 6 |
|---|---|---|---|---|---|---|---|---|---|---|---|---|---|
| Patient input (Mobility calendar) | 1 | 1 | 1 | 1 | 1 | 1 | 1 | 1 | 1 | 1 | 1 | 1 | 1 |
| Doctor Parameters | A1 | A2 | A3 | a | b | | | | A1 for sleep, A2 for sit, A3 for walk | | | | |
| | 1 | 2.2 | 3.3 | 1.3 | 2 | | | | a = master volume control; b = bolus volume control | | | | |
| Patient mobility in parametric terms | 1 | 1 | 1 | 1 | 1 | 1 | 1 | 1 | 1 | 1 | 1 | 1 | 1 |
| Infusion Rates ml/hr | 1.3 | 1.3 | 1.3 | 1.3 | 1.3 | 1.3 | 1.3 | 1.3 | 1.3 | 1.3 | 1.3 | 1.3 | 1.3 |
| Bolus (transient) | 0 | 0 | 0 | 0 | 0 | 0 | 0 | 0 | 0 | 0 | 0 | 0 | 0 |
| Half hours of a day | 6.5 | 7 | 7.5 | 8 | 8.5 | 9 | 9.5 | 10 | 10.5 | 11 | 11.5 | 12 | 12.5 |
| Patient Input (Mobility calendar) | 1 | 1 | 1 | 1 | 2 | 2 | 2 | 2 | 2 | 3 | 3 | 2 | 2 |
| Patient mobility in parametric terms | 1 | 1 | 1 | 1 | 2.2 | 2.2 | 2.2 | 2.2 | 2.2 | 3.3 | 3.3 | 2.2 | 2.2 |
| Infusion Rates ml/hr | 1.3 | 1.3 | 1.3 | 1.3 | 2.86 | 2.86 | 2.86 | 2.86 | 2.86 | 4.29 | 4.29 | 2.86 | 2.86 |
| Bolus (transient) | 0 | 0 | 0 | 3.12 | 0 | 0 | 0 | 0 | 2.86 | 0 | −2.86 | 0 | 0 |
| Half hours of a day | 13 | 13.5 | 14 | 14.5 | 15 | 15.5 | 16 | 16.5 | 17 | 17.5 | 18 | 18.5 | 19 |
| Patient input (Mobility calendar) | 2 | 2 | 2 | 1 | 1 | 1 | 1 | 1 | 2 | 2 | 2 | 2 | 2 |
| Patient mobility in parametric terms | 2.2 | 2.2 | 2.2 | 1 | 1 | 1 | 1 | 1 | 2.2 | 2.2 | 2.2 | 2.2 | 2.2 |
| Infusion Rates ml/hr | 2.86 | 2.86 | 2.86 | 1.3 | 1.3 | 1.3 | 1.3 | 1.3 | 2.86 | 2.86 | 2.86 | 2.86 | 2.86 |
| Bolus (transient) | 0 | 0 | −3.12 | 0 | 0 | 0 | 0 | 3.12 | 0 | 0 | 0 | 0 | 0 |
| Half hours of a day | 19.5 | 20 | 20.5 | 21 | 21 | 21.5 | 22 | 22.5 | 23 | 23.5 | 24 | | |
| Patient Input (Mobility calendar) | 2 | 3 | 3 | 2 | 2 | 2 | 2 | 2 | 2 | 2 | 2 | | |
| Patient mobility in parametric terms | 2.2 | 3.3 | 3.3 | 2.2 | 2.2 | 2.2 | 2.2 | 2.2 | 2.2 | 2.2 | 2.2 | | |
| Infusion Rates ml/hr | 2.86 | 4.29 | 4.29 | 2.86 | 2.86 | 2.86 | 2.86 | 2.86 | 2.86 | 2.86 | 2.86 | | |

TABLE 1-continued

| | | | | | | | | | | | |
|---|---|---|---|---|---|---|---|---|---|---|---|
| Bolus (transient) | 2.86 | 0 | −2.86 | 0 | 0 | 0 | 0 | 0 | 0 | 0 | 0 |

| | | |
|---|---|---|
| Half hours of a day Patient Input (Mobility calendar) | | |
| Patient mobility in parametric terms | SUM | TOTAL Volume per day |
| Infusions Rates ml/hr | 111.54 | 58.89 |
| Bolus (transient) | 3.12 | |

1 = sleep 2 = sit 3 = walk

| | | | | | |
|---|---|---|---|---|---|
| Patient feedback | | hyperkinesia in walk (Activity level 3) | | | |
| New Doctor Parameters | | reduce A3 | | | |
| | A1 | A2 | A3 | a | b |
| | 1 | 2.2 | _2.9_ | 1.3 | 2 |

New

| Half hours of a day | 0 | 0.5 | 1 | 1.5 | 2 | 2.5 | 3 | 3.5 | 4 | 4.5 | 5 | 5.5 | 6 |
|---|---|---|---|---|---|---|---|---|---|---|---|---|---|
| Patient mobility in parametric terms | 1 | 1 | 1 | 1 | 1 | 1 | 1 | 1 | 1 | 1 | 1 | 1 | 1 |
| Infusion Rates ml/hr | 1.3 | 1.3 | 1.3 | 1.3 | 1.3 | 1.3 | 1.3 | 1.3 | 1.3 | 1.3 | 1.3 | 1.3 | 1.3 |
| Bolus (transient) | 0 | 0 | 0 | 0 | 0 | 0 | 0 | 0 | 0 | 0 | 0 | 0 | 0 |

| | |
|---|---|
| Bold letters | Input Patient and doctor |
| _Italic letters_ | Pump calc and output (infusion) — Combination of 2 inputs and formula |
| Underlined letters | Correction after user feedback |

New

| Half hours of a day | 6.5 | 7 | 7.5 | 8 | 8.5 | 9 | 9.5 | 10 | 10.5 | 11 | 11.5 | 12 | 12.5 |
|---|---|---|---|---|---|---|---|---|---|---|---|---|---|
| Patient mobility in parametric terms | 1 | 1 | 1 | 1 | 2.2 | 2.2 | 2.2 | 2.2 | 2.2 | _2.9_ | _2.9_ | 2.2 | 2 2 |
| Infusion Rates ml/hr | 1.3 | 1.3 | 1.3 | 1.3 | 2.86 | 2.86 | 2.86 | 2.86 | 2.86 | 3.77 | 3.77 | 2.86 | 2.86 |
| Bolus (transient) | 0 | 0 | 0 | 3.12 | 0 | 0 | 0 | 0 | 1.82 | 0 | −1.82 | 0 | 0 |

New

| Half hours of a day | 13 | 13.5 | 14 | 14.5 | 15 | 15.5 | 16 | 16.5 | 17 | 17.5 | 18 | 18.5 | 19 |
|---|---|---|---|---|---|---|---|---|---|---|---|---|---|
| Patient mobty in parametric terms | 2.2 | 2.2 | 2.2 | 1 | 1 | 1 | 1 | 1 | 2.2 | 2.2 | 2.2 | 2.2 | 2.2 |
| Infusion Rates ml/hr | 2.86 | 2.86 | 2.86 | 1.3 | 1.3 | 1.3 | 1.3 | 1.3 | 2.86 | 2.86 | 2.86 | 2.86 | 2.86 |
| Bolus (transient) | 0 | 0 | −3.12 | 0 | 0 | 0 | 0 | 3.12 | 0 | 0 | 0 | 0 | 0 |

New

| Half hours of a day | 19.5 | 20 | 20.5 | 21 | 21 | 21.5 | 22 | 22.5 | 23 | 23.5 | 24 |
|---|---|---|---|---|---|---|---|---|---|---|---|
| Patient mobility in parametric terms | 2.2 | 2.9 | 29 | 2.2 | 2.2 | 2.2 | 2.2 | 2.2 | 2.2 | 2.2 | 2.2 |
| Infusion Rates ml/hr | 2.86 | 3.77 | 3.77 | 2.86 | 2.86 | 2.86 | 2.86 | 2.86 | 2.86 | 2.86 | 2.86 |
| Bolus (transient) | 1.82 | 8 | −1.82 | 0 | 0 | 0 | 0 | 0 | 0 | 0 | 0 |

| | | |
|---|---|---|
| New Patient mobility in parametric terms | SUM | Total volume per day |
| Infusion Rates ml/hr | 109.46 | 57.85 |
| Bolus (transient) | 3.12 | |

Patient feedback All OK!

EXPLANATIONS

First input to pump is patient's calendar as graph representing line "patient's input". More activity levels can be added such as intermediate to sit and walk, more than walk as gardening etc.

Second input to pump is "doctor's parameters"

The pump associates a parameter A1-A3 to each correspondent activity level of calendar i.e.

Formula is $$Et=a*At+b*(At+z-At)$$

Infusion Basal Rate is calculated according to formula's first term in lines "infusion rates"

Bolus here is a shot at 100 ml/hr additional infusion to the Basal Rate

A negative Bolus means we reduce rate until this volume is lost from ongoing infusion Bolus is given half an hour before transition as drug needs this time to react in the body Parameter a is a master Volume control, to change easily all levels in case patient needs more or less drug overall not in one specific activity If a=1 then all activity levels A are in ml/hr as in all pumps today

The invention claimed is:

1. A system for administering a drug to a Parkinson's disease patient comprising (a) a drug, (b) a storing bag for the drug, (c) a pump for administering the drug, and (d) a pump controller for controlling the pump activity,
the pump controller having access to a correlation of a first parameter $t_x$ and a second parameter $A_t$, to a current first parameter $t_x$, and to a mobility calendar indicating start and finish times for particular values of the first parameter $t_x$,
wherein the first parameter $t_x$ is correlated with an activity level of the patient and the second parameter $A_t$ is correlated with a dosage of the drug and the pump controller controls a flow rate of the drug based on changes of the first parameter $t_x$ scheduled in the mobility calendar of the first parameter $t_x$ and the correlation of the first parameter $t_x$ and the second parameter $A_t$; and
wherein the controller further has access to a parameter "b", wherein the controller controls the pump activity in case of a change of the first parameter by a multiplication of parameter b with the difference between an adjusted second parameter $A_{t+z}$ that is correlated with an adjusted first parameter t+z after the change and the second parameter $A_t$ that is correlated with the first parameter $t_x$ before the change to amend the dosage z minutes prior to the change by adding the result of the multiplication $b*(A_{t+z}-A_t)$ to the dosage according to the second parameter $A_t$, wherein z is the time delay of the drug action being constant for each different drug and infusion path.

2. The system according to claim 1, wherein the storing bag for the drug comprises internal micro-striation texture.

3. The system according to claim 1, wherein the system comprises (f) at least one sensor for therapy feedback measurement and report and/or (g) recording and monitoring infusion, and/or (h) at least one sensor for remote therapy regiment adjustment.

4. The system according to claim 1, wherein the controller further has access to a parameter "a" for a master volume control, wherein the controller controls the pump activity by a multiplication of the parameter a with the second parameter $A_t$ that is correlated with the first parameter $t_x$.

5. The system according to claim 1, wherein the controller further has access to a parameter "a" for a master volume control, wherein the controller controls the pump activity by a multiplication of the parameter a with the second parameter $A_t$ that is correlated with the first parameter $t_x$;
wherein the system is arranged in a way that the first parameter $t_x$ can be amended by the patient while parameters a, b and $A_t$ can be amended by an attending physician and/or by a control system that is in contact with the system.

6. The system according to claim 1, wherein the system further comprises an interface for submitting data to a remote control system and/or a remote data storage unit and/or an attending physician and/or wherein the system further comprises an interface for receiving data from a remote control system and/or a remote data storage unit and/or the attending physician.

7. The system according to claim 1, wherein the system further comprises at least one sensor for measurement of the status of the patient.

8. The system according to claim 7, wherein the at least one sensor for measurement of the status of the patient are selected from the group consisting of a 3D accelerometer, a gyroscope, an electromyogram, and a bed foil with sensing of movement, heart rate and/or respiration during sleep capability.

9. The system according to claim 8, having a sensor for movement measurement which is done in vicinity of a proximity sensor that is activated when two wrists come close together or a button is pressed on a wrist band.

10. The system according to claim 7, wherein the at least one sensor for measurement of the status of the patient are selected from the group consisting of a 3D accelerometer, a gyroscope, and an electromyogram.

11. The system according to claim 1, wherein the system comprises a patient's feedback function which comprises an input interface for a response of the patient to questions asked by the patient's feedback function.

12. The system according to claim 1, comprising a sensor for detecting malfunction of the system.

13. The system according to claim 1, wherein the system is arranged in a way that in case of negative feedback by the patient, critical status of the patient and/or malfunction of the system the respective information is automatically submitted to a remote control system and/or a remote data storage unit and/or an attending physician.

14. The system according to claim 1, wherein the drug comprises Levodopa and/or Carbidopa and/or benserazide suspended in a viscous liquid having a viscosity of 300±30 mPa-s measured at a moderate shear rate.

15. The system according to claim 1, wherein the drug is apomorphine.

16. The system according to claim 1, further comprising a catheter for delivering the drug to the digestive tract or the nasal cavity.

17. The system according to claim 1, wherein the storing bag for the drug is suitable for pre-filling and long-term oxidations-free storage has a multi layer wall with the internal layer made of ethylene vinyl acetate (EVA) or cyclic polyolefines and at least one further layer made of ethylene vinyl alcohol (EVOH).

18. The system according to claim 1, wherein, starting z minutes prior to the start time of a new activity, (i) when the activity level of the new activity is higher than the initial activity level, the flow rate of the drug is increased above a maintenance flow rate of the drug for the new activity, (ii) when the activity level of the new activity is lower than the initial activity level, the flow rate of the drug is decreased below a maintenance flow rate of the drug for the new activity, or (iii) both option (i) and option (ii), wherein z is the time delay of the drug action being constant for each different drug and infusion path.

19. The system according to claim 1, wherein the user is the patient or an assistant.

20. The system according to claim 1, wherein the drug comprises Levodopa and/or Carbidopa and/or benserazide in the form of microscopic particles.

21. The system according to claim 1, wherein the system is adapted to allow a user to schedule and/or update the particular values of the first parameter $t_x$ in the mobility calendar.

* * * * *